United States Patent
Lv et al.

(10) Patent No.: US 11,401,223 B2
(45) Date of Patent: Aug. 2, 2022

(54) SOLID COMPOSITE STABILIZER FOR PERCHLOROETHYLENE (PCE) AND PREPARATION METHOD

(71) Applicant: SINOPHARM CHEMICAL REAGENT CO., LTD., Shanghai (CN)

(72) Inventors: Wenhua Lv, Shanghai (CN); Xiaolan Wu, Shanghai (CN); Huiyi Lu, Shanghai (CN); Jianguo Guo, Shanghai (CN)

(73) Assignee: SINOPHARM CHEMICAL REAGENT CO., LTD., Shanghai (CN)

( * ) Notice: Subject to any disclaimer, the term of this patent is extended or adjusted under 35 U.S.C. 154(b) by 0 days.

(21) Appl. No.: 17/600,114

(22) PCT Filed: Feb. 2, 2021

(86) PCT No.: PCT/CN2021/074743
§ 371 (c)(1),
(2) Date: Sep. 30, 2021

(87) PCT Pub. No.: WO2021/232854
PCT Pub. Date: Nov. 25, 2021

(65) Prior Publication Data
US 2022/0144732 A1  May 12, 2022

(30) Foreign Application Priority Data

May 19, 2020  (CN) .......................... 202010425978.8

(51) Int. Cl.
*C07C 17/42* (2006.01)
(52) U.S. Cl.
CPC .................................. *C07C 17/42* (2013.01)
(58) Field of Classification Search
CPC .................................................... C07C 17/42
See application file for complete search history.

(56) References Cited

U.S. PATENT DOCUMENTS 6,534,688 B2 * 3/2003 Klausmeyer ............ C07C 17/42
570/264
2005/0049442 A1 3/2005 Gorton et al.

FOREIGN PATENT DOCUMENTS

| CN | 106011907 A | 10/2016 |
| EP | 0101047 A1 | 2/1984 |
| WO | 2007011444 A1 | 1/2007 |

OTHER PUBLICATIONS

Paquette, Leo A., Encyclopedia of Reagents for Organic Synthesis, 2009, Wiley.
Su Yuqin, et al. Synthesis and Performance of Macroporous Anion Exchange Resin, Journal of Beijing University of Aeronautics and Astronautics, 2003, pp. 493-496, vol. 29 (6).
Mao Pan, Study on the Stability of Tetrachloroethylene, 1986, Chlor-Alkali Industry.

* cited by examiner

*Primary Examiner* — Jafar F Parsa
(74) *Attorney, Agent, or Firm* — Bayramoglu Law Offices LLC

(57) ABSTRACT

The solid composite stabilizer for PCE includes the following components in parts by weight: 10 to 30 parts of a phenol-substituted ion-exchange resin, 50 to 80 parts of a basic anion-exchange resin, and 50 to 100 parts of a desiccating agent. The phenol-substituted ion-exchange resin is chloromethylated macroporous polystyrene-divinylbenzene (PS-DVB) substituted by a phenolic compound; and the basic anion-exchange resin is chloromethylated macroporous PS-DVB substituted by an amine compound. The preparation method includes the following step: thoroughly mixing the phenol-substituted ion-exchange resin, the basic anion-exchange resin, and the desiccating agent in a specified ratio to obtain the solid composite stabilizer for PCE. The solid composite stabilizer for PCE is packaged in a glass fiber bag and placed in PCE for storage and use.

17 Claims, 1 Drawing Sheet

SOLID COMPOSITE STABILIZER FOR PERCHLOROETHYLENE (PCE) AND PREPARATION METHOD

CROSS REFERENCE TO THE RELATED APPLICATIONS

This application is the national phase entry of International Application No. PCT/CN2021/074743, filed on Feb. 2, 2020, which is based upon and claims priority to Chinese Patent Application No. 202010425978.8, filed on May 19, 2020, the entire contents of which are incorporated herein by reference.

TECHNICAL FIELD

The present disclosure relates to the technical field of perchloroethylene (PCE) stabilization, and in particular to a solid composite stabilizer for PCE and a preparation method thereof.

BACKGROUND

PCE is a colorless liquid with a slight ether odor, and is widely used in the dry cleaning of fabrics and the metal degreasing due to its unique characteristics. However, there are very serious issues in the production, use, and storage of PCE because PCE is extremely unstable. Unstabilized PCE will decompose under the influence of air, light, heat, moisture, and metal, resulting in increased acidity and deteriorated PCE quality. Furthermore, deteriorated PCE will damage and contaminate fiber structures of fabrics, corrode related devices, and lose the original mild ether odor and produce a pungent odor. After PCE is stagnant for a long time, there will be yellow-green dewdrops on the walls of a bottle with the PCE (even vapors can be seen when a bottle stopper is pulled out), and the PCE is strongly acidic.

The instability of PCE is related to a molecular structure of PCE. Carbon-carbon double bonds in PCE molecules can be broken due to oxygen, light, heat, moisture, and other external factors, which promotes the decomposition of PCE. There are currently two decomposition mechanisms. The first decomposition mechanism is oxidative decomposition, which is shown in the following reaction equation:

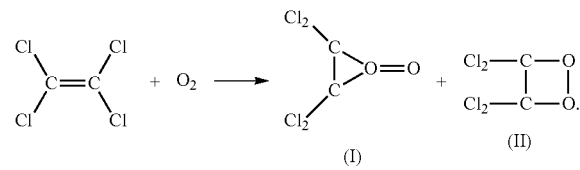

In the presence of air (oxygen), light, heat, and moisture (especially oxygen), a double bond of PCE is broken, and then is combined with oxygen to form an intermediate peroxide (I) and a compound (II), wherein the intermediate peroxide (I) undergoes molecular rearrangement to generate trichloroacetyl chloride and oxygen, and the compound (II) is further decomposed into phosgene (carbonyl chloride) with high molecular activity. The decomposition of the intermediate compound is accelerated by light and heat, especially by ultraviolet (UV) rays. In a wet solvent, trichloroacetyl chloride and phosgene are hydrolyzed into trichloroacetic acid (TCA), hydrogen chloride, and carbon dioxide. Apparently, if metals are present in the system, metal chlorides will inevitably be generated, and these decomposition products and light are catalysts for the decomposition reaction, which promotes the decomposition reaction to proceed continuously. The second decomposition mechanism is polycondensation decomposition, wherein when PCE is in contact with a metal chloride at a high temperature, the metal chloride serves as a catalyst to accelerate the polycondensation decomposition of PCE, so as to produce a tar-like polymer and hydrogen chloride. PCE for rinsing or dry cleaning will inevitably contact with metals at a high temperature.

PCE is typically decomposed by the first decomposition mechanism, but the second decomposition mechanism is still feasible. With PCE is decomposing, an acidity of a solvent increases significantly, and a hydrogen chloride gas overflows. The decomposition products of PCE were very complex, including organic acids, inorganic acids, phosgene, carbon oxides, polymers, and so on. Therefore, a stabilizer for effectively preventing the decomposition of PCE according to the above two mechanisms should have the function of inhibiting both the oxidative decomposition and the polycondensation decomposition. Generally, an antioxidant is used to prevent the oxidative decomposition, and an acid acceptor or a deactivator capable of deactivating metals and metal chlorides can be used to prevent the polycondensation decomposition.

Chinese patent 201610389109.8 discloses a stabilizer for PCE, including the following components: triethanolamine (TEA), n-pentane, chlorobutanol, butylene oxide, and thymol; and the stabilizer is used in PCE at an amount of 0.02 wt % to 0.041 wt %. However, the composition stabilizer is in liquid form and thus is not easy to separate from PCE after being mixed with PCE. No matter how much the stabilizer is added to PCE, an infrared radiation (IR) spectrum of the PCE will be affected somewhat, and IR impurities are introduced, which will eventually lead to unqualified PCE products.

SUMMARY

In order to solve the technical problem that after being mixed with PCE, the existing stabilizer is not easy to separate from PCE, results in IR impurities, and leads to an unqualified product, the present disclosure provides a solid composite stabilizer for PCE and a preparation method thereof. The solid composite stabilizer for PCE of the present disclosure is immiscible with PCE, does not affect a purity of PCE, does not result in IR impurities, and shows a prominent stabilizing effect for PCE (a stabilizing effect for PCE can last for more than 18 months).

To achieve the above objective, the present disclosure is implemented by the following technical solutions.

A solid composite stabilizer for PCE is provided, including the following components in parts by weight: 10 to 30 parts of a phenol-substituted ion-exchange resin, 50 to 80 parts of a basic anion-exchange resin, and 50 to 100 parts of a desiccating agent.

Further, the phenol-substituted ion-exchange resin may be a first substitution product from a reaction of a phenolic compound with chloromethylated macroporous polystyrene-divinylbenzene (PS-DVB); and the chloromethylated macroporous PS-DVB may have a benzyl chloride content of 12 wt % to 15 wt %.

Furthermore, the first substitution product may be obtained by washing with water, methanol, and absolute methanol and drying, and the first substitution product may have a moisture content of ≤50 ppm and an undetectable methanol residue.

Preferably, the phenolic compound may be a hydroquinone monosodium salt. The phenolic compound can also be other phenolic compounds, such as phenol, resorcinol, or catechol or a salt thereof. A first substitution product obtained by using the hydroquinone monosodium salt as a substituent to substitute a chloride ion of the ion-exchange resin exhibits better antioxidation and stabilization performance for PCE than a first substitution product obtained from other phenolic compounds.

Further, the basic anion-exchange resin may be a second substitution product from a reaction of an amine compound with chloromethylated macroporous PS-DVB; and the chloromethylated macroporous PS-DVB may have a benzyl chloride content of 12 wt % to 15 wt %.

Furthermore, the second substitution product may be obtained by washing with water, methanol, and absolute methanol and drying, and the second substitution product may have a moisture content of ≤50 ppm and an undetectable methanol residue.

Preferably, the amine compound may be ethylenediamine (EDA). Another organic amine compound can also be used as a substituent to substitute a chloride ion of the ion-exchange resin. Considering the cost and effect, a second substitution product prepared with EDA as a substituent exhibits better deacidification performance for PCE than a second substitution product prepared from other organic amine compounds.

Further, the desiccating agent may be a 4 A molecular sieve. The 4 A molecular sieve is easy to obtain and has a low cost.

Chloromethylated macroporous PS-DVB is a solid ion-exchange resin, which has a low cost and is easy to obtain. Chloromethylated macroporous PS-DVB can easily undergo a substitution reaction to obtain a first substitution product (obtained from a reaction of a phenolic compound with the chloromethylated macroporous PS-DVB) and a second substitution product (obtained from a reaction of an amine compound with the chloromethylated macroporous PS-DVB), and these substitution products have a low cost and an excellent effect. In addition, the substitution products of the ion-exchange resin are insoluble in PCE and will not affect the intrinsic physical and chemical properties of PCE. A composition of the substitution products of the ion-exchange resin and the molecular sieve has a smaller specific gravity than PCE, thus floats in a PCE liquid, and is easy to fully contact with the PCE liquid to play a role.

In another aspect, the present disclosure provides a preparation method of the solid composite stabilizer for PCE, including the following step: thoroughly mixing the phenol-substituted ion-exchange resin, the basic anion-exchange resin, and the desiccating agent in a specified ratio to obtain the solid composite stabilizer for PCE, where the solid composite stabilizer for PCE is packaged in a glass fiber bag and placed in PCE for storage and use.

Further, the solid composite stabilizer for PCE may be used at an amount of 0.5 wt % to 1.0 wt % per 500 mL of PCE.

BENEFICIAL TECHNICAL EFFECTS

In a preparation process of PCE, PCE will inevitably be contaminated by a trace amount of moisture in the environment, and during storage, the trace amount of moisture may undergo a free radical reaction with oxygen to produce an acyl chloride compound, and the acyl chloride compound further reacts with moisture to produce an acid, causing deterioration of PCE. The hydroxyl of the acid will cause IR absorption, and thus the PCE cannot reach the IR absorption index of environmentally-friendly reagents due to IR impurities. The substituted phenol on the phenol-substituted ion-exchange resin in the solid composite stabilizer of the present disclosure can capture free radicals generated in the above process and inhibit the reaction of the trace amount of moisture with oxygen to generate free radicals; the molecular sieve can absorb and remove the trace amount of moisture to suppress the formation of acid in the above process; and if an acid is inevitably produced in the above process, the amine compound substituent on the basic anion-exchange resin can react with the acid to form a salt, and the salt is adsorbed on the macroporous PS-DVB ion-exchange resin and does not affect the optical properties of PCE, thereby ensuring the quality of PCE.

According to quality standards, a shelf life of environmentally-friendly PCE is 6 months, and the stabilization of the solid composite stabilizer of the present disclosure for PCE can make a shelf life of environmentally-friendly PCE be more than 18 months. The solid composite stabilizer of the present disclosure can eliminate the free radicals of PCE during storage, scavenge produced deterioration substances such as acid anhydride or acid, and maintain the dryness of a PCE product. The solid composite stabilizer of the present disclosure is insoluble in PCE, and thus does not affect the critical optical (IR) quality and density of a PC product. The solid composite stabilizer of the present disclosure is packaged in a glass fiber bag, which is convenient for use and separation. In addition, the solid composite stabilizer of the present disclosure is easy to prepare, and the phenol-substituted ion-exchange resin and basic anion-exchange resin can be obtained by subjecting a conventional ion-exchange resins to a substitution reaction, which can be produced on a large scale.

DETAILED DESCRIPTION OF THE EMBODIMENTS

The technical solutions in the examples of the present disclosure are clearly and completely described below with reference to the examples of the present disclosure. Apparently, the described examples are merely some rather than all of the examples of the present disclosure. The following description of at least one exemplary example is merely illustrative, and not intended to limit the present disclosure and application or use thereof in any way. All other examples obtained by a person of ordinary skill in the art based on the examples of the present disclosure without creative efforts shall fall within the protection scope of the present disclosure.

Unless otherwise specified, the numerical values set forth in these examples do not limit the scope of the present disclosure. The techniques and methods known to those of ordinary skill in the relevant arts may not be discussed in detail, but where appropriate, the techniques and methods should be regarded as part of the description. In all examples shown and discussed herein, any specific value should be interpreted as merely exemplary, rather than restrictive. Therefore, other examples of the exemplary examples may have different values.

In addition, it should be noted that the use of the terms "first" and "second" to define a substitution product is merely for the convenience of distinguishing and naming the substitution products obtained from a reaction of chloromethylated macroporous PS-DVB with a phenolic compound and a reaction of chloromethylated macroporous PS-DVB with an amine compound. The first substitution product is obtained from the reaction of chloromethylated macroporous PS-DVB with a phenolic compound, and the second substitution product is obtained from the reaction of chloromethylated macroporous PS-DVB with an amine compound. Unless otherwise stated, the above-mentioned terms "first" and "second" have no special meaning and thus cannot be understood as limiting the protection scope of the present disclosure.

The macroporous PS-DVB used in the following examples is an ion-exchange resin intermediate chloromethylated bead produced by Shanghai Resin Factory (chloromethylated macroporous PS-DVB), which has a benzyl chloride content of 12 wt % to 15 wt % and a particle size of 60 to 100 mesh.

In the following examples, 6 m, 9 m, and 18 m in Tables 1, 2, and 3 represent 6 months, 9 months, and 18 months, respectively; and a blank indicates PCE without the solid composite stabilizer of the present disclosure.

Example 1

A solid composite stabilizer for PCE was provided, including the following components in parts by weight: 10 parts of a phenol-substituted ion-exchange resin, 80 parts of a basic anion-exchange resin, and 50 parts of a 4 A molecular sieve.

Figure 1:
FIG. 1 shows a synthesis route of a first substitution product from a reaction of a hydroquinone monosodium salt with chloromethylated macroporous PS-DVB.

The phenol-substituted ion-exchange resin was a first substitution product of a reaction of a hydroquinone monosodium salt with chloromethylated macroporous PS-DVB, and this reaction was a substitution reaction conducted according to the synthesis route shown in FIG. 1. A specific preparation method refers to the synthesis method of "Wang Resin" in *Encyclopedia of Reagents for Organic Synthesis* (author: Paquette, Leo A.). The first substitution product obtained was called 4-hydroxyphenol resin (HP) for short. The first substitution product was washed with water, methanol, and absolute methanol and then vacuum-dried, such that the first substitution product had a moisture content of ≤50 ppm and an undetectable methanol residue.

Figure 2:
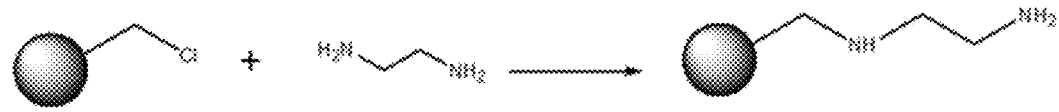
FIG. 2 shows a synthesis route of a second substitution product from a reaction of EDA with chloromethylated macroporous PS-DVB.

The basic anion-exchange resin was a second substitution product of a reaction of EDA with chloromethylated macroporous PS-DVB, and this reaction was a substitution reaction conducted according to the synthesis route shown in FIG. 2. A specific preparation method refers to the "Amination Reaction" in *"Preparation and Properties of Macroporous Anion-Exchange Resin"* (Su Yuqin, Zhang Zuoguang, *"Journal of Beijing University of Aeronautics and Astronautics"*, 2003, Volume 29 (6): 493-496). The second substitution product obtained was called EDA resin (EAP) for short. The second substitution product was washed with water, methanol, and absolute methanol and then vacuum-dried, such that the second substitution product had a moisture content of ≤50 ppm and an undetectable methanol residue.

A preparation method of the above solid composite stabilizer for PCE included the following step: the above-mentioned phenol-substituted ion-exchange resin (the first substitution product), the basic anion-exchange resin (the second substitution product), and the 4 A molecular sieve were thoroughly mixed in a specified ratio to obtain the solid composite stabilizer for PCE. The solid composite stabilizer for PCE was packaged in a glass fiber bag and placed in PCE for storage and use.

Usage: 500 mL (about 815 g) of fresh environmentally-friendly PCE was taken and placed in a brown bottle, 4.1 g (0.50 wt %) of the solid composite stabilizer was added, and then the brown bottle was sealed and packaged.

Results of the quality assurance experiment were shown in Table 1.

TABLE 1

Test results of the solid composite stabilizer of Example 1

| Test item | Standards for environmentally-friendly PCE HJ637-2018 (Ministry of Environmental Protection) Test standard | Blank | Blank (6 m) | Blank (9 m) | After stabilization (6 m) | After stabilization (18m) |
|---|---|---|---|---|---|---|
| Content, % ≥ | 99.5 | 99.9 | 99.9 | 99.9 | 99.9 | 99.9 |
| Moisture (H$_2$O), % ≤ | 0.05 | 0.04 | 0.04 | 0.04 | 0.03 | 0.03 |
| Density (20° C.), g/cm$^3$ | 1.63 | Qualified | Qualified | Qualified | Qualified | Qualified |
| Refractive index, % | 1.5 | Qualified | Qualified | Qualified | Qualified | Qualified |
| Outer packaging | 500 mL/4 L | | | | | |
| Absorbance (IR, with a 4 mm empty cuvette as reference), nm | | | | | | |
| 2,930 cm$^{-1}$ | 0.34 | 0.28 | 0.31 | 0.35 | 0.28 | 0.28 |
| 2,960 cm$^{-1}$ | 0.07 | 0.04 | 0.05 | 0.08 | 0.04 | 0.05 |
| 3,030 cm$^{-1}$ | 0.00 | 0.00 | 0.00 | 0.01 | 0.00 | 0.00 |

Example 2

A solid composite stabilizer for PCE was provided, including the following components in parts by weight: 30 parts of a phenol-substituted ion-exchange resin, 50 parts of a basic anion-exchange resin, and 100 parts of a 4 A molecular sieve.

The phenol-substituted ion-exchange resin was a first substitution product of a reaction of a hydroquinone monosodium salt with chloromethylated macroporous PS-DVB, and this reaction was a substitution reaction conducted according to the synthesis route shown in FIG. 1. A specific preparation method refers to the synthesis method of "Wang Resin" in *"Encyclopedia of Reagents for Organic Synthesis"* (author: Paquette, Leo A.). The first substitution product obtained was called 4-hydroxyphenol resin (HP) for short. The first substitution product was washed with water, methanol, and absolute methanol and then vacuum-dried, such that the first substitution product had a moisture content of ≤50 ppm and an undetectable methanol residue.

The basic anion-exchange resin was a second substitution product of a reaction of EDA with chloromethylated macroporous PS-DVB, and this reaction was a substitution reaction conducted according to the synthesis route shown in FIG. 2. A specific preparation method refers to the "Amination Reaction" in *"Preparation and Properties of Macroporous Anion-Exchange Resin"* (Su Yuqin, Zhang Zuoguang, *"Journal of Beijing University of Aeronautics and Astronautics"*, 2003, Volume 29 (6): 493-496). The second substitution product obtained was called EDA resin (EAP) for short. The second substitution product was washed with water, methanol, and absolute methanol and then vacuum-dried, such that the second substitution product had a moisture content of ≤50 ppm and an undetectable methanol residue.

A preparation method of the above solid composite stabilizer for PCE included the following step: the above-mentioned phenol-substituted ion-exchange resin, the basic anion-exchange resin, and a desiccating agent were thoroughly mixed in a specified ratio to obtain the solid composite stabilizer for PCE. The solid composite stabilizer for PCE was packaged in a glass fiber bag and placed in PCE for storage and use.

Usage: 500 mL (about 815 g) of fresh environmentally-friendly PCE was taken and placed in a brown bottle, 8.2 g (1.0 wt %) of the solid composite stabilizer was added, and then the brown bottle was sealed and packaged.

Results of the quality assurance experiment were shown in Table 2.

Example 3

A solid composite stabilizer for PCE was provided, including the following components in parts by weight: 20 parts of a phenol-substituted ion-exchange resin, 65 parts of a basic anion-exchange resin, and 70 parts of a 4 A molecular sieve.

The phenol-substituted ion-exchange resin was a first substitution product of a reaction of a hydroquinone monosodium salt with chloromethylated macroporous PS-DVB, and this reaction was a substitution reaction conducted according to the synthesis route shown in FIG. 1. A specific preparation method refers to the synthesis method of "Wang Resin" in *"Encyclopedia of Reagents for Organic Synthesis"* (author: Paquette, Leo A.). The first substitution product obtained was called 4-hydroxyphenol resin (HP) for short. The first substitution product was washed with water, methanol, and absolute methanol and then vacuum-dried, such that the first substitution product had a moisture content of ≤50 ppm and an undetectable methanol residue.

The basic anion-exchange resin was a second substitution product of a reaction of EDA with chloromethylated macroporous PS-DVB, and this reaction was a substitution reaction conducted according to the synthesis route shown in FIG. 2. A specific preparation method refers to the "Amination Reaction" in *"Preparation and Properties of Macroporous Anion-Exchange Resin"* (Su Yuqin, Zhang Zuoguang, *"Journal of Beijing University of Aeronautics and Astronautics"*, 2003, Volume 29 (6): 493-496). The second substitution product obtained was called EDA resin (EAP) for short. The second substitution product was washed with water, methanol, and absolute methanol and then vacuum-dried, such that the second substitution product had a moisture content of ≤50 ppm and an undetectable methanol residue.

A preparation method of the above solid composite stabilizer for PCE included the following step: the above-mentioned phenol-substituted ion-exchange resin, the basic anion-exchange resin, and a desiccating agent were thoroughly mixed in a specified ratio to obtain the solid composite stabilizer for PCE. The solid composite stabilizer for PCE was packaged in a glass fiber bag and placed in PCE for storage and use.

TABLE 2

Test results of the solid composite stabilizer of Example 2

| Test item | Standards for environmentally-friendly PCE HJ637-2018 (Ministry of Environmental Protection) Test standard | Example 2 Test results of the solid composite stabilizer (measured) | | | | |
|---|---|---|---|---|---|---|
| | | Blank | Blank (6 m) | Blank (9 m) | After stabilization (6 m) | After stabilization (18m) |
| Content, % ≥ | 99.5 | 99.9 | 99.9 | 99.9 | 99.9 | 99.9 |
| Moisture ($H_2O$), % ≤ | 0.05 | 0.04 | 0.04 | 0.04 | 0.02 | 0.02 |
| Density (20° C.), $g/cm^3$ | 1.63 | Qualified | Qualified | Qualified | Qualified | Qualified |
| Refractive index, % | 1.5 | Qualified | Qualified | Qualified | Qualified | Qualified |
| Outer packaging | 500 mL/4 L | | | | | |
| Absorbance (IR, with a 4 mm empty cuvette as reference), nm | | | | | | |
| 2,930 $cm^{-1}$ | 0.34 | 0.28 | 0.31 | 0.35 | 0.27 | 0.28 |
| 2,960 $cm^{-1}$ | 0.07 | 0.04 | 0.05 | 0.08 | 0.04 | 0.04 |
| 3,030 $cm^{-1}$ | 0.00 | 0.00 | 0.00 | 0.01 | 0.00 | 0.00 |

Usage: 500 mL (about 815 g) of fresh environmentally-friendly PCE was taken and placed in a brown bottle, 6.4 g (0.75 wt %) of the solid composite stabilizer was added, and then the brown bottle was sealed and packaged.

Results of the quality assurance experiment were shown in Table 3.

TABLE 3

Test results of the solid composite stabilizer of Example 3

| Test item | Standards for environmentally-friendly PCE HJ637-2018 (Ministry of Environmental Protection) Test standard | Example 3 Test results of the solid composite stabilizer (measured) | | | | |
|---|---|---|---|---|---|---|
| | | Blank | Blank (6 m) | Blank (9 m) | After stabilization (6 m) | After stabilization (18m) |
| Content, % ≥ | 99.5 | 99.9 | 99.9 | 99.9 | 99.9 | 99.9 |
| Moisture ($H_2O$), % ≤ | 0.05 | 0.04 | 0.04 | 0.04 | 0.02 | 0.03 |
| Density (20° C.), g/cm$^3$ | 1.63 | Qualified | Qualified | Qualified | Qualified | Qualified |
| Refractive index, % | 1.5 | Qualified | Qualified | Qualified | Qualified | Qualified |
| Outer packaging | 500 mL/4 L | | | | | |
| Absorbance (IR, with a 4 mm empty cuvette as reference), nm | | | | | | |
| 2,930 cm$^{-1}$ | 0.34 | 0.28 | 0.31 | 0.35 | 0.27 | 0.29 |
| 2,960 cm$^{-1}$ | 0.07 | 0.04 | 0.05 | 0.08 | 0.04 | 0.04 |
| 3,030 cm$^{-1}$ | 0.00 | 0.00 | 0.00 | 0.01 | 0.00 | 0.00 |

It can be seen from the above Tables 1, 2, and 3 that, on month 9, the IR absorbance indexes of the blank sample (9 m) without the solid composite stabilizer of the present disclosure at 2,930 cm$^{-1}$, 2,960 cm$^{-1}$, and 3,030 cm$^{-1}$ were higher than the test standards, indicating that the PCE had deteriorated on month 9; after 0.50 wt % to 1 wt % of the solid composite stabilizer of the present disclosure was added to PCE for stabilization, the IR absorbance indexes of the PCE (18 m) at 2,930 cm$^{-1}$, 2,960 cm$^{-1}$, and 3,030 cm$^{-1}$ were all lower than the test standards, indicating that the solid composite stabilizer of the present disclosure exhibited a prominent stabilization effect for PCE, which lasted for 18 months; and the addition of the solid composite stabilizer of the present disclosure did not affect the density of PCE, and during the stabilization process, the solid composite stabilizer of the present disclosure floated in the PCE liquid.

The foregoing description only provides preferred specific implementations of the present disclosure, and the protection scope of the present disclosure is not limited thereto. Any equivalent replacement or modification made according to the technical solution and inventive concept by a person skilled in the art within a technical scope of the present disclosure shall fall within the protection scope of the present disclosure.

What is claimed is:

1. A solid composite stabilizer for perchloroethylene (PCE), comprising the following components in parts by weight: 10 to 30 parts of a phenol-substituted ion-exchange resin, 50 to 80 parts of a basic anion-exchange resin, and 50 to 100 parts of a desiccating agent.

2. The solid composite stabilizer for PCE according to claim 1, wherein the phenol-substituted ion-exchange resin is a first substitution product from a reaction of a phenolic compound with chloromethylated macroporous polystyrene-divinylbenzene (PS-DVB); and the chloromethylated macroporous PS-DVB has a benzyl chloride content of 12 wt % to 15 wt %.

3. The solid composite stabilizer for PCE according to claim 2, wherein the first substitution product is obtained by washing with water, methanol, and absolute methanol and drying, and the first substitution product has a moisture content of ≤50 ppm and methanol residues are not detected in the first substitution product.

4. The solid composite stabilizer for PCE according to claim 2, wherein the phenolic compound is a hydroquinone monosodium salt.

5. The solid composite stabilizer for PCE according to claim 1, wherein the basic anion-exchange resin is a second substitution product from a reaction of an amine compound with chloromethylated macroporous PS-DVB; and the chloromethylated macroporous PS-DVB has a benzyl chloride content of 12 wt % to 15 wt %.

6. The solid composite stabilizer for PCE according to claim 5, wherein the second substitution product is obtained by washing with water, methanol, and absolute methanol and drying, and the second substitution product has a moisture content of ≤50 ppm and methanol residues are not detected in the second substitution product.

7. The solid composite stabilizer for PCE according to claim 5, wherein the amine compound is ethylenediamine (EDA).

8. The solid composite stabilizer for PCE according to claim 1, wherein the desiccating agent is a 4 A molecular sieve.

9. A preparation method of the solid composite stabilizer for PCE according to claim 1, comprising the following step: thoroughly mixing the phenol-substituted ion-exchange resin, the basic anion-exchange resin, and the desiccating agent in a specified ratio to obtain the solid composite stabilizer, wherein the solid composite stabilizer is packaged in a glass fiber bag and placed in PCE for storage and use.

10. The preparation method according to claim 9, wherein the solid composite stabilizer used in the PCE has an amount of 0.5 wt % to 1.0 wt %.

11. The preparation method according to claim 9, wherein the phenol-substituted ion-exchange resin is a first substitution product from a reaction of a phenolic compound with chloromethylated macroporous polystyrene-divinylbenzene (PS-DVB); and the chloromethylated macroporous PS-DVB has a benzyl chloride content of 12 wt % to 15 wt %.

12. The preparation method according to claim 11, wherein the first substitution product is obtained by washing with water, methanol, and absolute methanol and drying, and the first substitution product has a moisture content of ≤50 ppm and methanol residues are not detected in the first substitution product.

13. The preparation method according to claim 11, wherein the phenolic compound is a hydroquinone monosodium salt.

14. The preparation method according to claim 9, wherein the basic anion-exchange resin is a second substitution product from a reaction of an amine compound with chloromethylated macroporous PS-DVB; and the chloromethylated macroporous PS-DVB has a benzyl chloride content of 12 wt % to 15 wt %.

15. The preparation method according to claim 14, wherein the second substitution product is obtained by washing with water, methanol, and absolute methanol and drying, and the second substitution product has a moisture content of ≤50 ppm and methanol residues are not detected in the second substitution product.

16. The preparation method according to claim 14, wherein the amine compound is ethylenediamine (EDA).

17. The preparation method according to claim 9, wherein the desiccating agent is a 4 A molecular sieve.

\* \* \* \* \*